United States Patent [19]

Ijitsu et al.

[11] Patent Number: 5,174,998
[45] Date of Patent: Dec. 29, 1992

[54] SUSTAINED RELEASE COMPOSITIONS USING AS MATRIX HEMICELLULOSE EXTRACTED FROM WHEAT BRAN

[75] Inventors: Takanori Ijitsu, Saitama; Kiwamu Shiiba, Kawagoe; Hiroyoshi Hara, Kawagoe; Yoshie Negishi, Saitama, all of Japan

[73] Assignee: Nisshin Flour Milling Co., Ltd., Tokyo, Japan

[21] Appl. No.: 759,713

[22] Filed: Sep. 12, 1991

Related U.S. Application Data

[63] Continuation of Ser. No. 442,945, Nov. 29, 1989, abandoned.

[30] Foreign Application Priority Data

Nov. 30, 1988 [JP] Japan .................. 63-301076

[51] Int. Cl.⁵ ............... A01N 25/08; A01N 25/34; A61F 2/02; A61K 9/20
[52] U.S. Cl. .................... 424/410; 424/405; 424/408; 424/409; 424/423; 424/424; 424/425; 424/451; 424/464; 424/474; 424/489; 514/781; 536/56; 536/128
[58] Field of Search .............. 424/405, 409, 413, 423, 424/424, 425, 408, 410, 451, 464, 474, 489; 514/781; 536/56, 128

[56] References Cited

U.S. PATENT DOCUMENTS 3,294,544 12/1966 Stanko .................. 424/410 X
4,857,505 8/1989 Arendt .................... 514/2

FOREIGN PATENT DOCUMENTS 58-41824  3/1983  Japan .
61-286330 12/1986 Japan .
62-120315 6/1987  Japan .
87-06241 10/1987 World Int. Prop. O. .

Primary Examiner—Thurman K. Page
Assistant Examiner—Carlos Azpuru
Attorney, Agent, or Firm—Michael N. Meller

[57] ABSTRACT

A sustained release composition containing a chemical substance in a matrix. The matrix substantially comprises a hemicellulose extracted from wheat bran under alkaline conditions or a wheat bran extract containing the hemicellulose. The chemical substance is released at a controlled rate from the composition over a long period of time.

5 Claims, 8 Drawing Sheets

SUSTAINED RELEASE COMPOSITIONS USING AS MATRIX HEMICELLULOSE EXTRACTED FROM WHEAT BRAN

This application is a continuation, of application Ser. No. 442,945, filed Nov. 29, 1989, abandoned.

BACKGROUND OF THE INVENTION

1. Field of the Invention

This invention relates to a sustained release composition. More particularly, it is concerned with a sustained release composition using a hemicellulose extracted from wheat bran or a wheat bran extract predominantly containing the hemicellulose as a matrix having a property of releasing a chemical substance at a controlled rate.

2. Description of the Prior Art

Various approaches have been proposed to develop sustained release preparations, that is, preparations for retarding release of the active ingredient to allow the effect to be sustained over a prolonged time. For example, there are employed many methods including binding of the active ingredient with a binder poor in disintegration in digestive tracts and coating of the active ingredient with such a material as wax or a macromolecular substance. Among the methods for preparing such sustained release preparations, a cellulose derivative have recently called attention particularly in view of its sustained release function. There are disclosed sustained release preparations using a lower alkyl ether of cellulose as the matrix (Japanese Patent LOP Publication No. 286330/1986) and sustained release preparations using hydroxypropyl methylcellulose or the like (Japanese Patent LOP Publication No. 120315/1987).

On one hand, many attempts have been made hitherto to isolate in pure form hemicellulose contained in wheat bran and effectively use it. For example, an invention relating to use as anticholesteremic agent of hemicellulose produced by extracting wheat bran under alkaline conditions has been proposed in Japanese Patent LOP Publication No. 41824/1983. We have proposed a method for extracting and purifying hemicellulose useful as fibrous food which comprises extracting wheat bran under weak alkaline conditions.

Since the cellulose derivatives used as a matrix in sustained release preparations of the prior art are semi-synthetic products obtained by chemical modification of naturally occurring cellulose, a naturally occurring substance substitutable therefor will be preferred in consideration of safety, toxicity and other factors.

The cellulose derivatives used in the prior art methods such as lower alkyl ethers of cellulose and hydroxypropyl methylcellulose are somewhat hygroscopic so that they are defective in that they will absorb moisture in the air while being formed, for example, into tablets to become sticky and coating such as sugar coating is needed in order to avoid such a defect.

Therefore, sustained release preparations free from such defects have been desired.

SUMMARY OF THE INVENTION

As a result of extensive studies with the object of solving the above-mentioned problems, we have found that a wheat bran extract predominantly containing a hemicellulose produced by extracting wheat bran under alkaline conditions and a hemicellulose purified from the extract are very valuable as a matrix for sustained release compositions.

The present invention is directed to a sustained release composition containing a chemical substance in a matrix, the matrix substantially comprising a hemicellulose extracted from wheat bran under alkaline conditions or a wheat bran extract containing the hemicellulose.

The hemicellulose and the wheat bran extract containing the same used in the invention are generically called hereafter "bran hemicellulose", for convenience' sake.

The sustained release compositions of the invention are useful not only as useful pharmaceutical agents utilizable in the pharmaceutical preparations for oral administration as well as in the drug delivery system (DDS) for local target therapy but also as sustained release pesticides in which bactericides or insecticides are used as the substance to be incorporated or as sustained release attractants for fish or insect or sustained release repellents for animal or insect in which the chemical substance is used as attractant or repellent to these living things. Further, the sustained release compositions of the invention can be applied to cosmetics, bath preparations and aromatics.

DETAILED DESCRIPTION OF THE INVENTION

Figure 1:
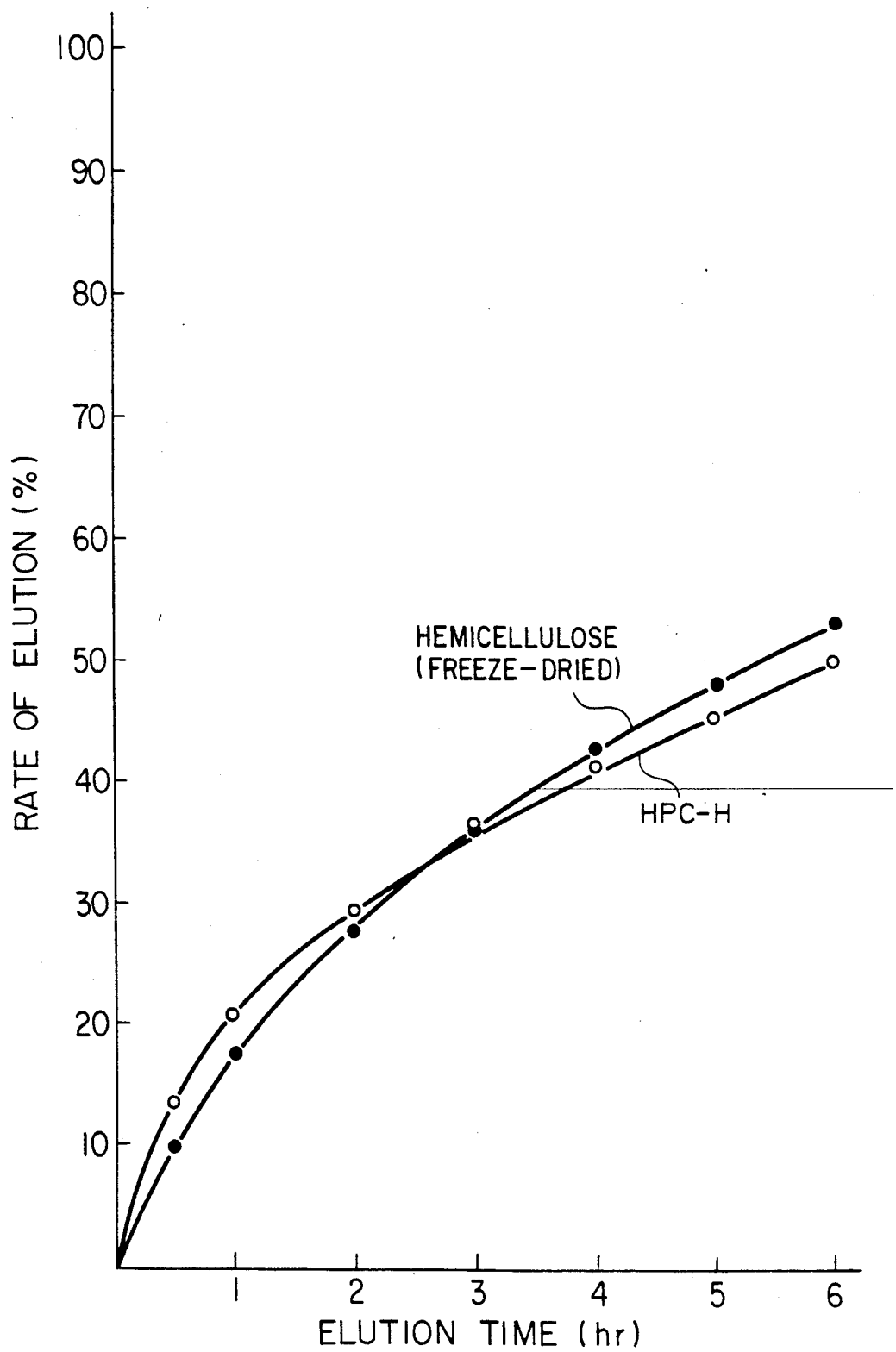
FIG. 1 shows results of the comparative elution test in elution time of di-chlorpheniramine maleate between the tablets using the bran hemicellulose of the invention as a matrix and the prior art tablets using hydroxypropyl cellulose as a matrix.

The bran hemicellulose used in the invention is prepared, for example, by washing wheat bran with water to remove water-soluble substances, then treating the washed bran preferably with an aqueous alkali solution in a lower concentration, e.g., of 0.1–0.4 N to dissolve a fraction principally composed of hemicellulose into the aqueous alkali solution, optionally neutralizing the aqueous solution with an acid, subsequently subjecting the resulting mass successively to purification by ultrafiltration or an ion exchanger and if necessary conducting freeze-drying or separation and drying of precipitates formed by addition of ethanol. The bran hemicellulose includes a bleached product of such hemicellulose as prepared above.

In addition to the one produced by extracting hemicellulose under such mild conditions as mentioned above, the bran hemicellulose used in the invention is also produced by treating wheat bran with an aqueous alkali solution in a higher concentration, e.g., 0.5N or higher to dissolve a fraction principally composed of hemicellulose into the aqueous alkali solution, neutralizing the aqueous solution with an acid and desalting the resulting solution by such means as dialysis or ion exchanger resin treatment followed by freeze-drying or separation and drying of precipitates formed by addition of ethanol.

According to the invention, it has been surprisingly found that use of the bran hemicellulose as a matrix for sustained release compositions can produce prominent effects that are not anticipatable by known matrixes for sustained release preparations.

As a matter of fact, it is considered that the bran hemicellulose exhibits high swellability when contacted with water, and such gel formation permits the chemical substance to be released at a controlled rate.

Nevertheless, the bran hemicellulose does not grow sticky with some water contained therein, and the tablets formed by tabletting are free from variations in hardness and are almost nonhygroscopic without absorption of water due to moisture in the air so that the formed products can be stored with high stability for a long period of time. Furthermore, it is observed that there is no variation in release of the substance due to variation in tabletting pressure and almost no pH dependency in releasing the substance.

In addition to excellent sustained release property and stability when formed into preparation, the bran hemicellulose is associated with almost no problems of toxicity and safety, because of its naturally occurring hemicellulose.

The chemical substances incorporated in the matrix of the invention are not limited to specific ones but may include any substances which are absorbable from digestive tracts or locally absorbable from stomatic mucosa, nasal mucosa or skin when given to animals including humans in the form of a sustained release preparation, or may include any of compounds added as coloring matters, perfumes, etc.

Examples of such substances as drugs are recited below.

Antiinflammatory and analogesic agents such as indomethacin, diclorfenac, ibuprofen, phenylbutazone, oxyphenbutazone, mepirizole, aspirin, ethenzamide, aminopyrine, phenacetin, etc;

antituberculous agents such as isoniazid, ethane butol hydrochloride, antibiotics, etc.;

coronary vasodilators such as isosorbide nitrate, nitroglycerin, nifedipine, etc.;

antihypertensive agents such as hydralazine hydrochloride, methyldopa, furosemide, spinronolactone, guanethiadine sulfate, reserpine, etc.;

psychotropic agents such as chlorpromazin hydrochloride, haloperidol, perphenazine, diazepam, etc.;

antihistaminics such as chlorpheniramine maleate, diphenhydramine hydrochloride, etc.;

vitamins such as thiamine nitrate, ascorbic acid, nicotinamide, etc.;

antigouty agents such as allopurinol, colchicine, probeecid, etc.,;

hypnotic and sedative agents such as amobarbital, bromvalerylurea, chloral hydrate, etc.;

anti-malignant tumoric agents such as fluorouracil, cyclophosphamide, thiotepa, etc.;

antidepressants such as phenylpropanolamine ephedrine, etc.;

diuretics such as hydrohlorothiazide, triamterene, etc.;

antidiabetics such as acetohexamide, insulin, tolubutamide, etc.;

bronchodilators such as aminophylline, theophylline, etc.;

antitussives such as codeine phosphate, noscapine, dextromethorphan, etc.;

narcotics such as morphine hydrochloride, cocaine hydrochloride, pethidine hydrochloride, etc.;

antiarrhythmic agents such as quinidine hydrochloride, digitoxin, digoxin, procainamide, etc.;

surface anesthelic agents such as ethyl aminobenzoate, lidocaine, dibucaine, etc.;

antiepileptic agents such as phenytoin, ethosuxmide, primidone, etc.; and synthetic adrenocorticosteroid such as hydrocortisone, prednisolone, triamcinolone, betamethasone, etc.

The sustained release composition containing the above substances in the matrix of the invention can be in any form including solid preparations such as tablets, pills, granules, capsules, powders and troche, semi-solid preparations such as ointment, cataplasm and lotion or liquid preparations such as suspension and elixir.

In preparing such solid, semi-solid or liquid preparations, additives commonly known in the art can optionally be added. Those additives include excipients, disintegrating agents, lubricants, flavoring agents, coloring agents, preservatives, surface active agents, etc.

The chemical substances which are used in the invention also include pesticides recited as follows:

Bactericides such as chloropicrin, etc.;

insecticides such as DDT, pyrethrins, organic phosphorus insecticides, BHT, etc.;

Rodenticides such as warfarin, etc.;

Herbicides such as 2,4-dichlorophenoxyacetic acid, 2,4,5-T, MCP, 4,6-dinitro-o-cresol sodium salt, etc., and Plant growth regulators such as naphthylacetic acid, etc.

Furthermore, the chemical substances used in the invention include attractants for fish and insect or repellents for animal and insect, which are recited as follows:

attractants and repellents such as amino acids, e.g., glutamine, methionine, alanine, serine, tyrosine, asparagine, cystein, etc.; and such as alcohols, e.g., $\beta$-phenyl alcohols, butyl alcohols, etc.;

fish attractants such as nucleic acid-related substances, e.g., 5'-ADP, 5'-IMP, 5'-UMP, etc.;

attractants such as isoeugenol, insect pheromones, etc., and noxious insect repellents such as dimethyl phthalate, dimethyl carbate, propyl N,N-diethylsuccinbelow. amidate, etc.

The composition of the present invention can also be applied to perfumes and coloring matters to be incorporated in cosmetics, aromatics and bath preparations.

Examples of such perfumes include:

hydrocarbons such as α-pinene, camphene, limonene and myrcene;

alcohols such as anise alcohol, geraniol, cinnamyl alcohol, menthol and linalool;

aldehydes such as phenylacetaldehyde, piperonal, citral, citronellal and cyclamen aldehyde;

ketones such as carvone, jasmine, civetone, muscone and α-ionone;

esters such as methyl salicylate and ethyl acetate;

phenol ethers such as eugenol, safrole and nerolin;

lactones such as coumalin; and natural perfumes such as funnel, calamus, camphor, cinnamon and mint.

The coloring matters include food tar colors used as food additive and natural coloring matters such as crocin, beet red, laccaic acid, cochineal, curcumine, chlorophyll, cacao color, riboflavin, caramel and α-carotene.

The bran hemicellulose used as a matrix in the sustained release compositions of the invention may be either a freeze-dried product or a dried ethanol precipitate product obtained by the above-described preparative method. From a standpoint of easiness in incorporation of the substances a powdered product of the ethanol precipitates which is higher in bulk density or a bleached product thereof is more preferable than the freeze-dried product which is more bulky and lower in specific gravity.

The sustained release rate of the present compositions can be controlled by varying a proportion of the matrix depending upon the characteristics of the chemical substance incorporated therein. The sustained release effect is observed in a proportion of at least 10% by weight of the matrix based on the total weight of the composition, preferably at least 20% exhibiting remarkable effect and at least 50% exhibiting more remarkable effect. The sustained release compositions can be formulated by merely mixing the bran hemicellulose and the chemical substance. Alternatively, both may be combined by dissolving the substance in a solvent, adding the solution to the bran hemicellulose and evaporating the solvent.

The sustained release rate of the present composition may be controlled by adding to the matrix a crystalline cellulose, preferably being naturally occurring, starch or the like in combination with the bran hemicellulose of the invention. Other sustained release matrixes conventionally used in the art may be employed in combination with the matrix of the present invention. Examples of such matrixes include hydroxypropyl methylcellulose, polyvinylpyrrolidone, polyvinyl alcohol, sodium polyacrylate, sodium alginate, guar gum, etc.

The invention is further illustrated by the following non-limitative examples.

The bran hemicellulose used in the following examples was prepared by the procedures described in the following Preparative Examples 1 and 2.

PREPARATIVE EXAMPLE 1

Preparation of a freeze-dried product of bran hemicellulose

A dispersion of 2 kg of refined bran (protein content of 16% by weight) in 20 lit. of warm water at 50° C. was stirred using Super F agitator manufactured by Nisshin Engineering Co., Ltd. at a circumferential speed of 25 m/sec. for 5 min. After completion of the agitation, solid matters were separated from the solution phase by means of a centrifugal filter (manufactured by Tanabe Tekko Co., Ltd.). The solid matters thus obtained (water content of ca. 50%, protein content of 33% by weight) weighing ca. 3 kg were placed in 20 lit. of 0.2N aqueous solution of sodium hydroxide at 70° C., and the mixture was stirred using the same agitator as above at a circumferential speed of 20 m/sec. for 90 min.

The resulting solution was centrifuged at 5000×g for 10 min. After centrifugation the supernatant was separated and diluted with water to a saccharide level of 5 ml/ml. Temperature of the solution was maintained at 50° C. The entire solution was treated under conditions of a pressure of 8 kg f/cm$^2$ and a flow rate of 13 lit./min. for 3 hours while passing through a tabular ultrafiltration membrane NTU 3520 (model P-18, membrane surface of 0.76 m$^2$, inner diameter of 11.5 mm) manufactured by Nitto Denko Co., Ltd. Water in the same amount as that of the solution that had passed through the membrane was supplemented into the tube during this operation to maintain a constant amount of the liquid to be treated with the membrane.

Water supply was stopped after 3 hours, and concentration started under the same conditions as above (flow rate of 13 lit./min., pressure of 8 kg f/cm$^2$). The concentration was carried out without consideration of the decrease in flux to a saccharide concentration of the aqueous solution of ca. 10 mg/ml (ca. 1.5 hours). The treated solution was passed through 500 cc of cation exchange resin IR-120E manufactured by Organo Co., Ltd. at a flow rate 10 times as much the volume of the ion-exchange resin per hour and then through anion-exchange resin IRA-93 manufactured by the same company at the same flow rate. The aqueous solution after the ion-exchange resin treatments was freeze-dried (at a temperature of 30° C. under a degree of vacuum of 0.1 Torr or below) to obtain ca. 150 g of a white product.

PREPARATIVE EXAMPLE 2

Ethanol precipitates of bran hemicellulose

A dispersion of 2 kg of refined bran (protein content of 16% by weight) in 20 lit. of warm water at 50° C. was stirred using Super F agitator manufactured by Nisshin Engineering Co., Ltd. at a circumferential speed of 25 m/sec. for 5 min. After completion of the agitation, solid matters were separated from the solution phase by means of a centrifugal filter (manufactured by Tanabe Tekko Co., Ltd.). The solid matters thus obtained (water content of ca. 50%, protein content of 33% by weight) weighing ca. 3 kg were placed in 20 lit. of 0.2N aqueous solution of sodium hydroxide at 70° C., and the mixture was stirred using the same stirrer as above at a circumferential speed of 20 m/sec. for 90 min.

The resulting solution was centrifuged at 5000×g for 10 min. After centrifugation the supernatant was separated and diluted with water to a saccharide level of 5 ml/ml. Temperature of the solution was maintained at 50° C. The entire solution was treated under conditions of a pressure of 8 kg f/cm$^2$ and a flow rate of 13 lit./min. for 3 hours while passing through a tabular ultrafiltration membrane NTU 3520 (model P-18, membrane surface of 0.76 m$^2$, inner diameter of 11.5 mm) manufactured by Nitto Denko Co., Ltd. Water in the same amount as that of the solution that had passed through the membrane was supplemented into the tube during this operation to maintain a constant amount of the liquid to be treated with the membrane.

Water supply was stopped after 3 hours, and concentration started under the same conditions as above (flow rate of 13 lit./min., pressure of 8 kg f/cm$^2$). The concentration was carried out without consideration of the decrease in flux to a saccharide concentration of the aqueous solution of ca. 10 mg/ml (ca. 1.5 hours). The treated solution was passed through 500 cc of cation exchange resin IR-120E manufactured by Organo Co., Ltd. at a flow rate 10 times as much the volume of the ion-exchange resin per hour and then through anion-exchange resin IRA-93 manufactured by the same company at the same flow rate. To the aqueous solution after the ion-exchange resin treatments was added ethanol in an amount 4 times as much that of the solution followed by stirring. Precipitates thus formed were separated by means of a centrifuge. The separated precipitates were air-dried to completely evaporate the ethanol. The dried mass was ground by means of a grinder (manufactured by Letch Co., Ltd.) to obtain 135 g of powdery water-soluble hemicellulose.

EXAMPLE 1

Investigation was made on elution behavior using dl-chlorpheniramine maleate, an antihistaminic. Hydroxypropyl cellulose conventionally used at present (Nippon Soda, HPC-H) was used as control. A mixture of the following formulation was tabletted.

| (Control formulation) | | |
|---|---|---|
| dl-Chlorpheniramine maleate | | 60 mg |
| HPC-H | | 240 mg |
| | Total | 300 mg |
| (The present formulation) | | |
| dl-Chlorpheniramine maleate | | 60 mg |
| | Total | 300 mg |

The above formulations were respectively tabletted using a 8-mm punch-and-die at a tabletting pressure of 100 kg/cm$^2$. The tablets were tested for elution by the paddle as the elution test solution. Results are shown in FIG. 1. The rate of elution in 6 hours was the same with the control formulation and with the present formulation. The elution curve is substantially linear in terms of the relationship between time and rate of elution exhibiting nearly 0-order elution characteristic.

EXAMPLE 2

Investigation was made on elution according to Example 1 with β-starch (Junsei Sangyo, PC-1000) and HPC-H as control and bromphenol blue as a test substance.

Figure 2:
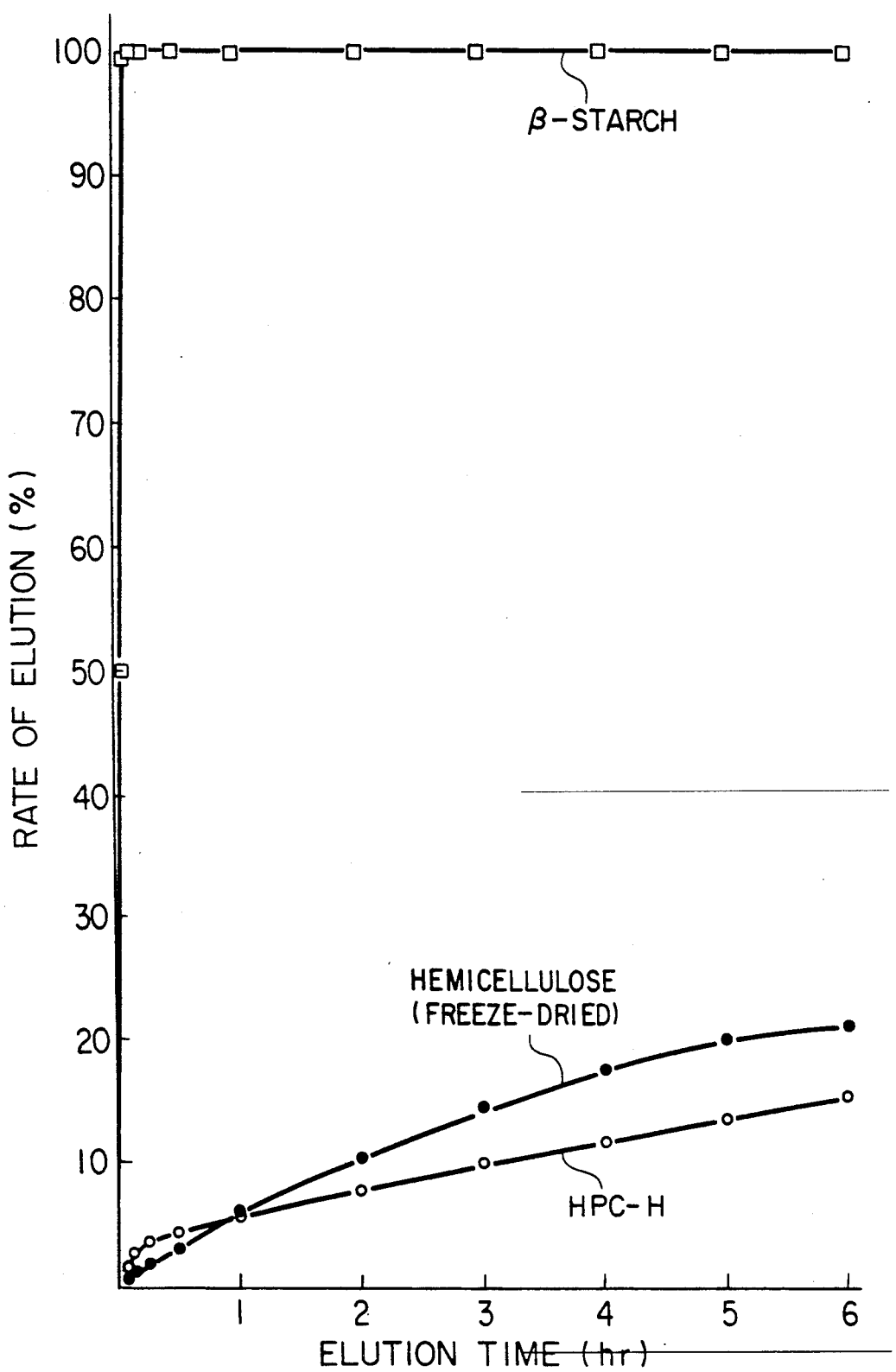
FIG. 2 shows results of a comparative elution test in elution time of bromphenol blue among the tablets using the bran hemicellulose of the invention as a matrix and those using as a matrix 8-starch and hydroxypropyl cellulose, respectively.

| (Control formulation) | | |
|---|---|---|
| Bromphenol blue | | 5 mg |
| β-starch | | 240 mg |
| | Total | 245 mg |
| Bromphenol blue | | 5 mg |
| HPC-H | | 240 mg |
| | Total | 245 mg |
| (The present formulation) | | |
| Bromphenol blue | | 5 mg |
| Freeze-dried bran hemicellulose | | 240 mg |
| | Total | 245 mg |

β-starch was eluted 100% from the tablet within 5 minutes. Sustained release effect was observed even after 6 hours when using HPC-H or the bran hemicellulose as a sustained release matrix. Results are shown in FIG. 2.

EXAMPLE 3

Using freeze-dried bran hemicellulose, ethanol-precipitated hemicellulose and HPC-H control, each 0.2 g was weighed and tabletted under 100 kg/cm$^2$. The tablets were allowed to stand in a thermo-hygrostatt at 45° and 75% for one week. Equilibrium moisture content was determined from changes in dried weight measured by an infrared moisture meter (Metler, LP16) as compared with the tablets at the start of storage in desiccator.

Figure 3:
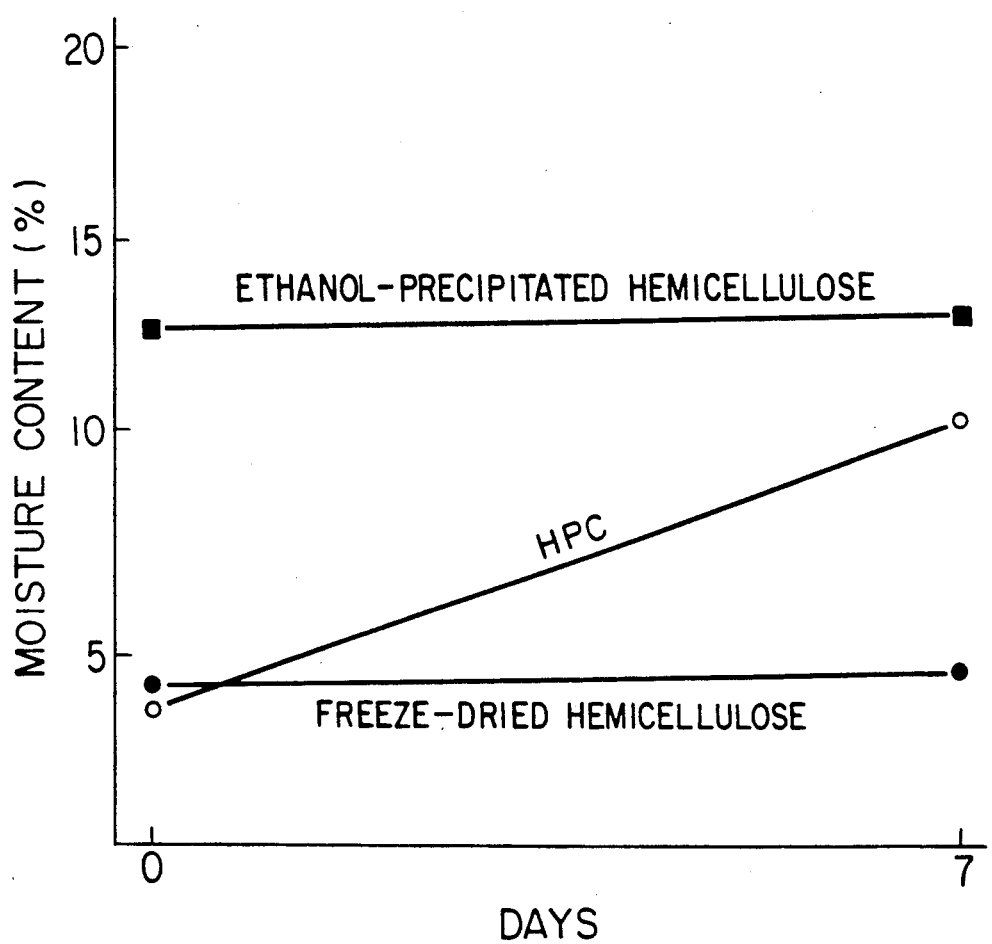
FIG. 3 shows results of a test of variations in equilibrium moisture content among the freeze dried bran hemicellulose, the ethanol-precipitated bran hemicellulose and hydroxypropyl cellulose.

Every point of measurement was expressed in terms of the mean in three trials. The results were shown in FIG. 3. There was observed almost no increase in moisture content with respect to the freeze-dried hemicellulose and the ethanol-precipitated hemicellulose, although the latter contained more moisture due to the method for the preparation than did the former. On the contrary, moisture content was increased with the HPC-H control to a level twice as high or higher than the start thereby indicating high hygroscopicity.

Changes in configuration were also remarkable after one week, particularly as indicated by increase in viscosity and attachment to the glass vessel was observed. In contrast, with both the freeze-dried and the ethanol-precipitated hemicelluloses, there were observed almost no change in moisture content as compared with the start as well as no change in configuration.

The above results suggest that use of the hemicellulose enables production of tablets with very small variations of the equilibrium moisture content associated and free from influence of the hygroscopicity. It is also expectable that stabilization is achieved by merely mixing and forming a compound poorly stable to moisture without using special formulation technique.

EXAMPLE 4

Figure 4:
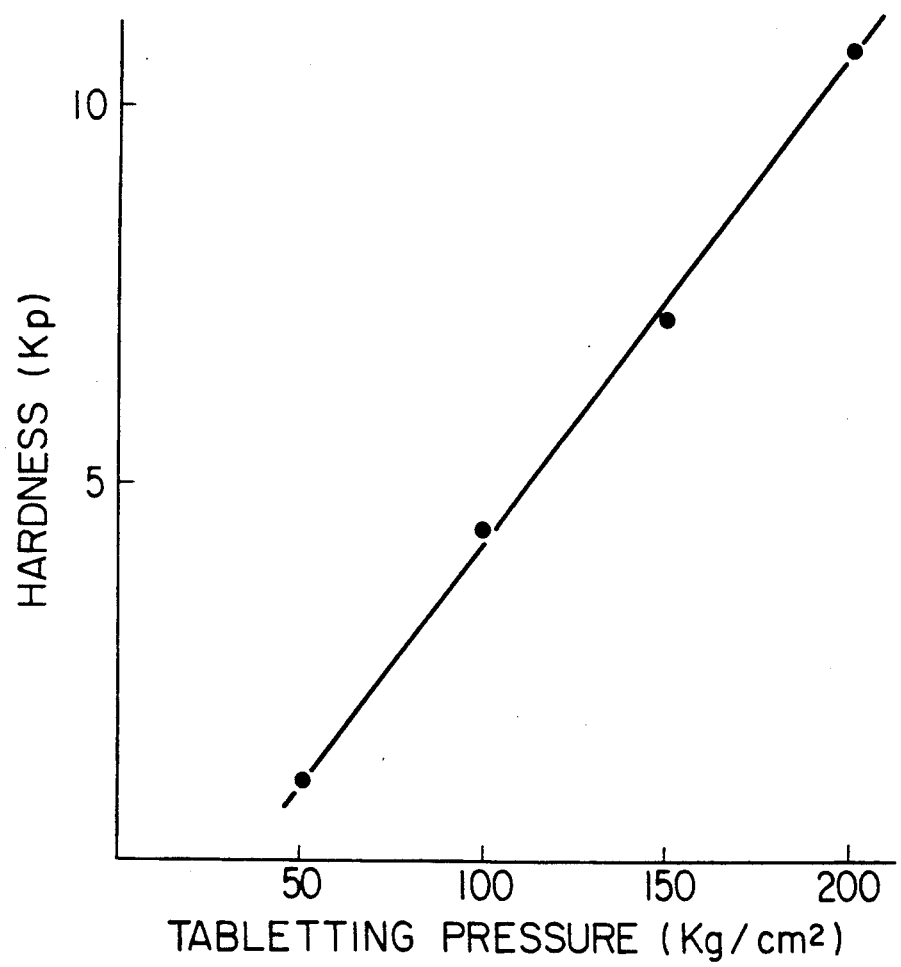
FIG. 4 is a graph indicating relationship between tabletting pressure and hardness of the tablets prepared from the ethanol-precipitated hemicellulose.

Tablets were prepared under varied tabletting pressure of 50, 100, 150 and 200 kg/cm$^2$, respectively from about 0.2 g of the ethanol-precipitated bran hemicellulose and tested for hardness using a tablet hardness meter (Schleuniger 2E). The results are shown in FIG. 4. There exists good linear relationship between tabletting pressure and hardness. When tabletting was made at more than 300 kg/cm$^2$, there was produced hardness of 20 kg/cm$^2$ or higher. With the freeze-dried product, hardness of 20 kg/cm$^2$ or higher was confirmed at a tabletting pressure of 100 kg/cm$^2$.

The above results indicates that tablets of an adequate hardness can be obtained by controlling the tabletting pressure.

Next, effect of the tabletting pressure on elution was investigated.

EXAMPLE 5

Figure 5:
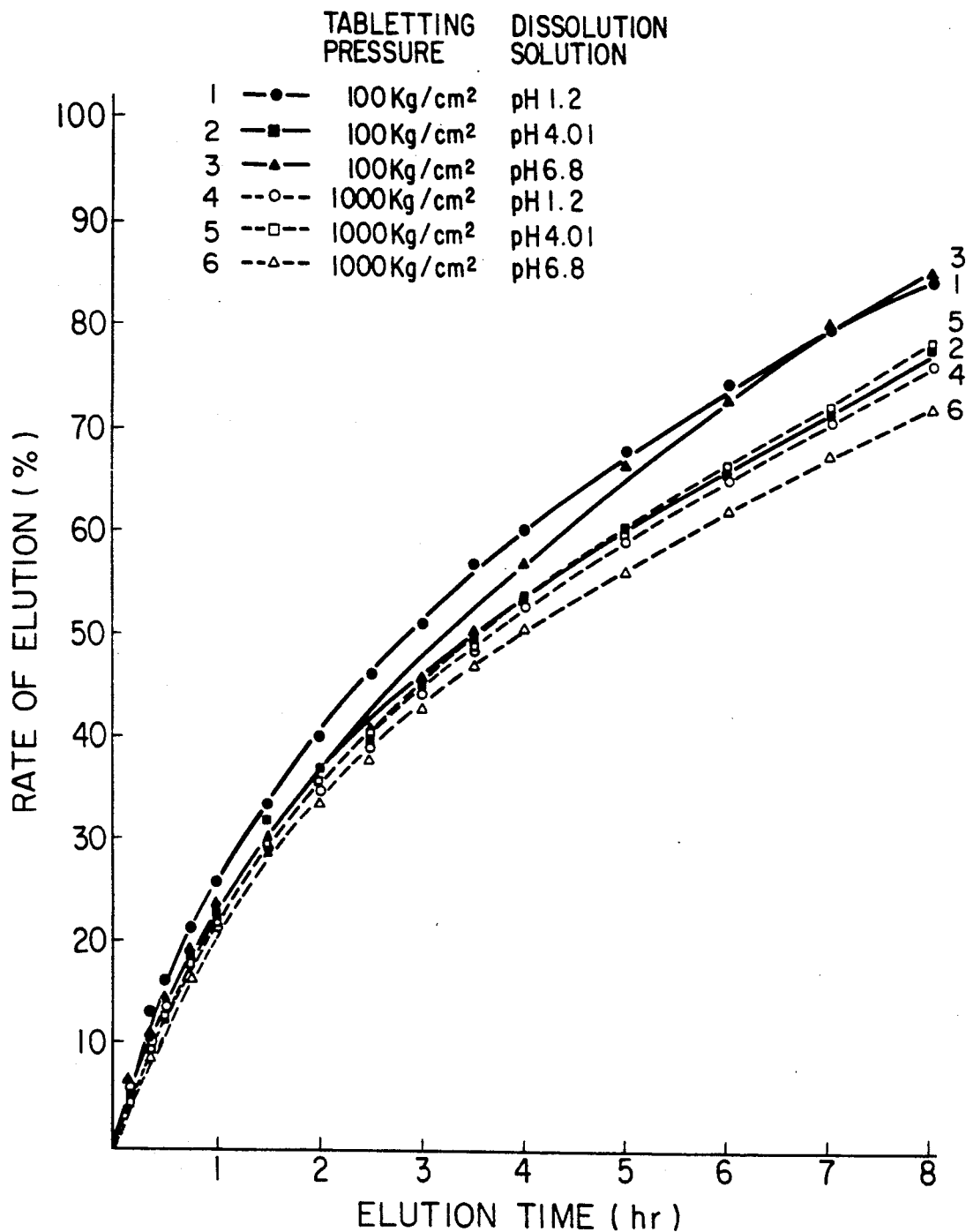
FIG. 5 shows results of the investigations on the effect of tabletting pressure and pH on elution of the substance which is a drawing indicating that an elution behavior is uniform independently of the tabletting pressure and the ph.

Effects of the tabletting pressure and nature of the elution test solution on a sustained release elution were investigated using theophylline, a bronchodilator. The results are shown in FIG. 5. The formulation was as follows:

| Theophylline | 10 mg |
|---|---|
| Ethanol-precipitated hemicellulose | 200 mg |

-continued

| | Total | 210 mg |

Tabletting pressure was set at 100 kg/cm² and 1000 kg/cm², respectively. Tabletting was made in three groups, and the tablets were eluted respectively at a pH of 1.2, 4.01 and 6.8. Comparison of the elution curves indicates that the difference in elution after 8 hours between the tabletting pressure is about 5% on average, that is, there can be almost no difference in elution between the tabletting pressures. This is advantageous from a standpoint of formulation technique. No difference in elution was observed due to the difference in pH, thus constant pH-independent elution being expectable. The elution test was carried out according to the elution test specified in Japanese Pharmacopoeia (11th edition) in which three test solutions at a pH of 1.2, 4.01 or 6.8 were selected and measurement was made by the paddle method (rotation of 100 rpm). The pH-independent compositions allows applications in a wide range not only for pharmaceuticals such as highly precisely controllable prolonged oral preparations but also for quasi-drugs and food products having a sustained release function.

EXAMPLE 6

The bran hemicellulose can also be used for releasing pesticides and fish attractants at a controlled rate.

A pesticide, 2,4-dichlorophenoxyacetic acid used as a herbicide in particular was selected, converted with sodium methoxide in methanol to the sodium salt, then dried and tabletted using the formulation shown below.

| (Formulation) | |
|---|---|
| Sodium 2,4-dichlorophenoxyacetate | 50 mg |
| Ethanol-precipitated bran hemicellulose | 200 mg |
| Total | 250 mg |
| Sodium 2,4-dichlorophenoxyacetate | 50 mg |
| β-starch | 200 mg |
| Total | 250 mg |

Similarly, inosinic acid which has a taste-stimulant effect in fish such as yellowtail and "moggo" was tabletted using the formulation as given below.

| Inosinic acid (5'-IMP) | 50 mg |
|---|---|
| Ethanol-precipitated bran hemicellulose | 200 mg |
| Total | 250 mg |
| Inosinic acid (5'-IMP) | 50 mg |
| β-starch | 200 mg |
| Total | 250 mg |

Figure 6:
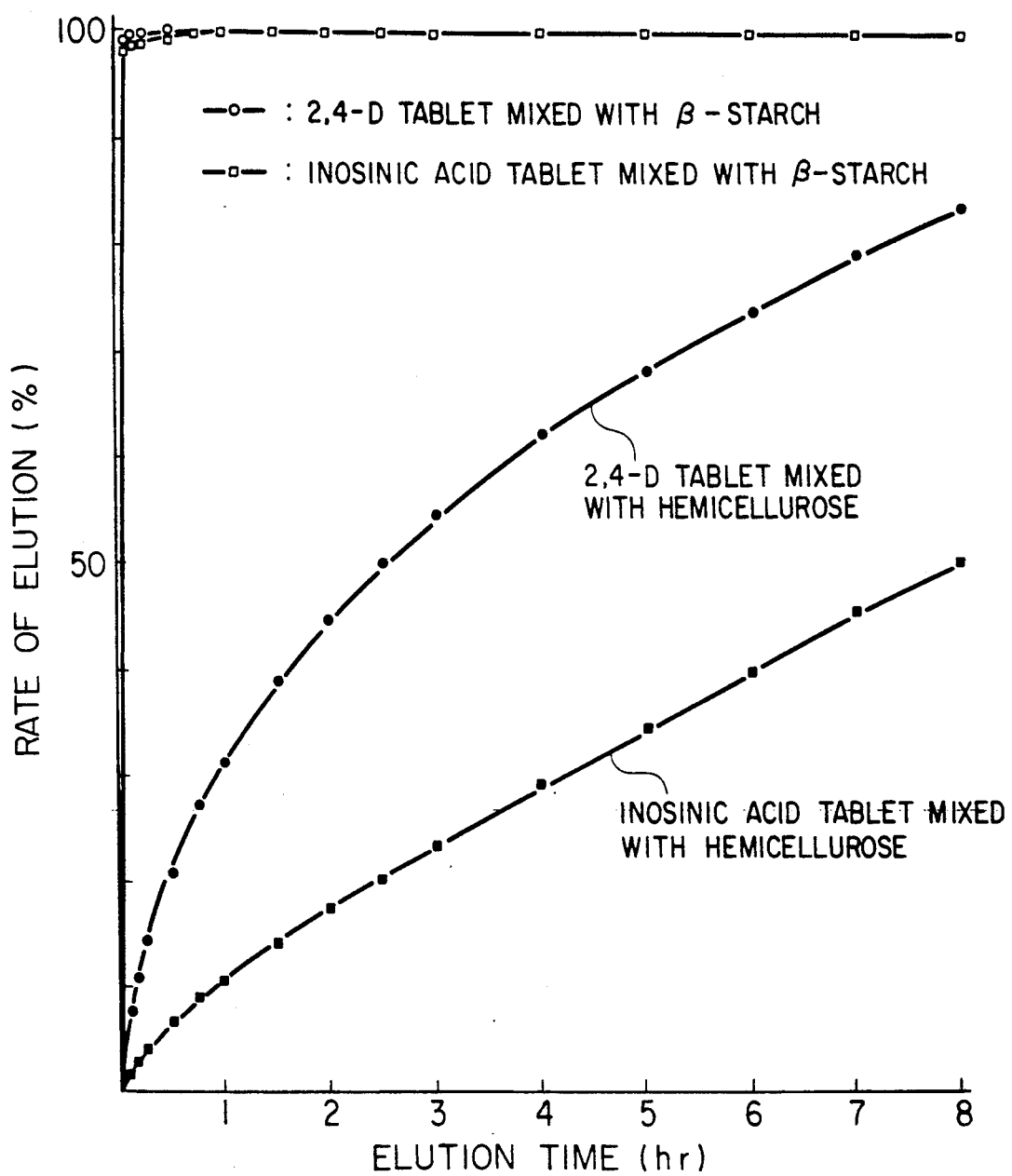
FIG. 6 is a drawing indicating a sustained release effect when sodium 2,4-dichlorophenoxyacetate and inosinic acid were respectively incorporated in the hemicellulose as compared with the effect when these agents were respectively incorporated in β-starch.

The above formulations were tabletted respectively at 100 kg/cm² and tested for elution with deionized water. The results are shown in FIG. 6. Both substances (2,4-dichlorophenoxyacetate and inosinic acid) were eluted 100% within 15 minutes from the tablets in which β-starch was contained as a matrix. In contrast, a sustained release effect of the substances was observed in the tablets wherein the hemicellulose was contained in a matrix.

According to the matrix of the present invention, there are gained advantages of allowing sustained release in pharmaceuticals, health foods, pesticides, fish attractants, etc., in which little effect is expected by prompt release as well as of stabilizing and other secondary effects.

EXAMPLE 7

Control of the rate of sustained release was attempted using as an example ascorbic acid frequently used in medicine or as an additive for health foods and food products.

Figure 7:
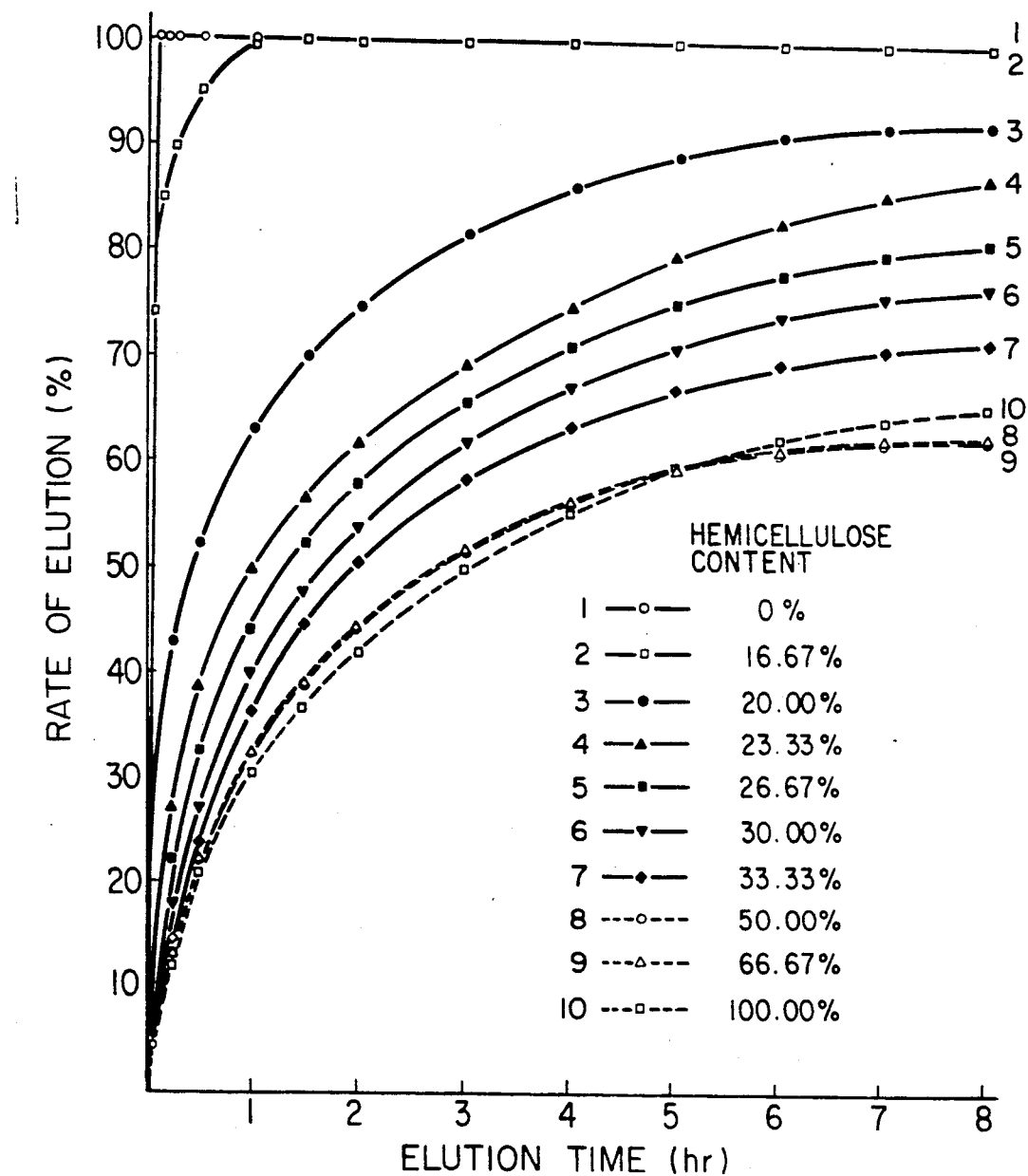
FIG. 7 is a drawing indicating a controlled release effect of L-ascorbic acid using a mixture of the hemicellulose and crystalline cellulose.

Crystalline cellulose (Abicel 301, Asahi Kasei Co., Ltd.) which is structurally close to hemicellulose and is of a natural type exhibited no sustained release effect at all. The material presently accepted in Japanese Pharmacopoeia (11th revision) is one used as binder, disintegrating agent, lubricant or the like. To 10 mg of ascorbic acid were respectively added 0, 0.05, 0.06, 0.07, 0.08, 0.09, 0.10, 0.15, 0.20 and 0.30 g of the hemicellulose and correspondingly 0.3, 0.25, 0.24, 0.23, 0.22, 0.21, 0.20, 0.15, 0.10 and 0 g of the crystalline cellulose and blended. The blend was directly pressed at a tabletting pressure of 200 kg/cm². The blend was directly pressed at a tabletting pressure of 200 kg/cm². The elution test was carried out according to the elution test specified in Japanese Pharmacopoeia (11th edition) using deionized water as test solution by the paddle method (rotation of 100 rpm). The results were shown in FIG. 7.

The elution in the absence of the hemicellulose reached 100% within one min. The content of the hemicellulose is 0, 16.67, 20.00, 23.33, 26.67, 30.00, 33.33, 50, 66.67 and 100% by weight, respectively, based on the weight of excipient. Ascorbic acid was eluted 100% in one hour with 16.67% hemicellulose content, but a sustained release effect was remarkable with 20% hemicellulose content. There is correlation between the proportion and the release in the range between 20% and 33.33% contents (that is, the release is controllable).

In contrast, approximately equal release curves were obtained in a hemicellulose content of 50% or more. This confirmed that the release was controllable by mixing the hemicellulose with other excipients in an adequate ratio. No substantial difference in sustained release effect was found in hemicellulose contents of 50% and higher. This can reduce the amount of tablets, granules, powders, etc., so that the drug is easy to take with commercial advantage.

EXAMPLE 8

Four male beagle dogs (weighing 10.0–12.0 kg) were orally administered respectively with tablets of a sustained release composition and a lactose composition in which 5-FU (fluorouracil) clinically used as anti-malignant tumoric agent was contained.

Per 50 mg of 5-FU was weighed 200 mg of the hemicellulose and lactose for direct press respectively for the composition followed by blending and tabletting at 70 kg/cm².

Figure 8:
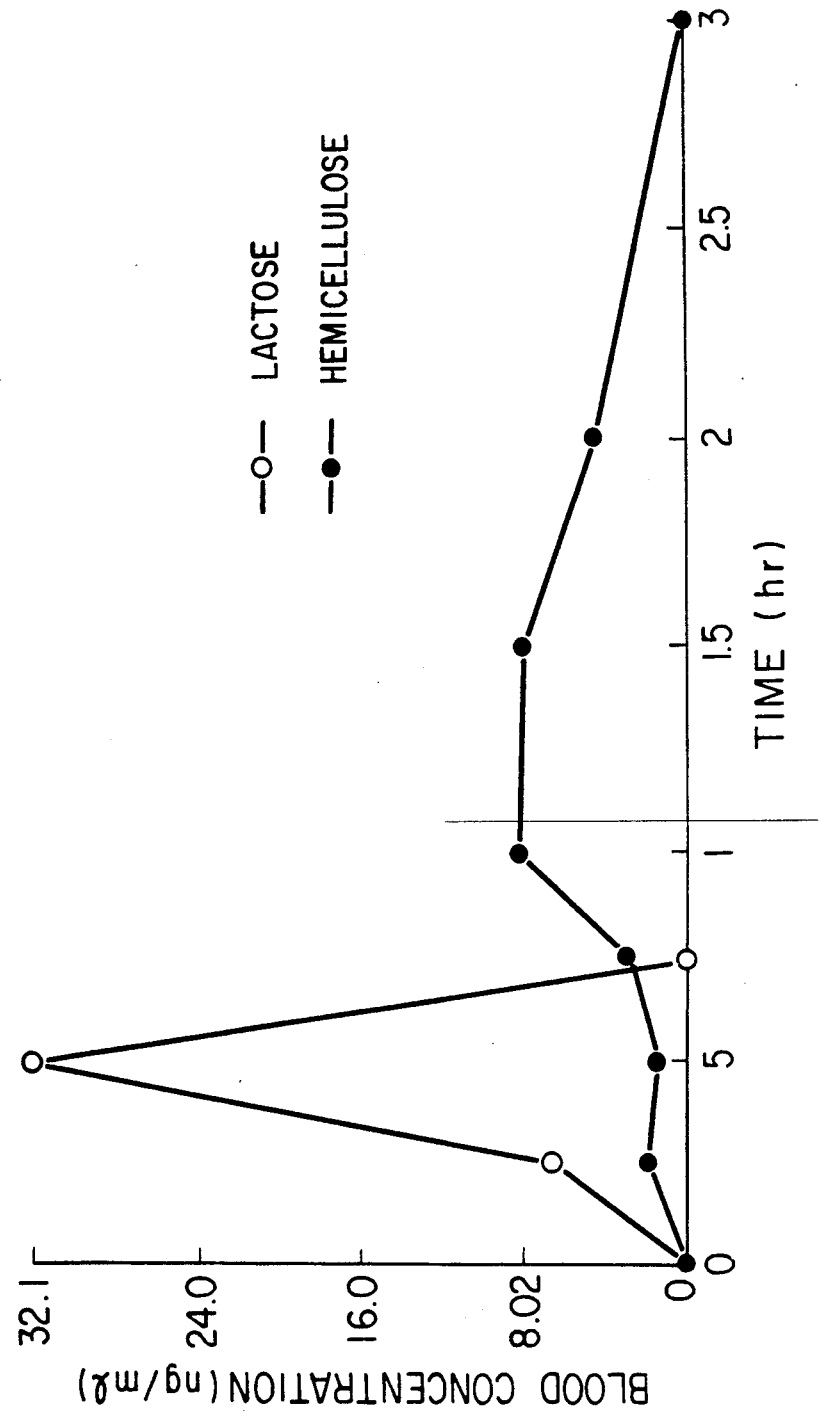
FIG. 8 is a drawing indicating changes in the blood concentration of 5-FU with time when a lactose tablet and a hemicellulose tablet were respectively given orally to the beagle dog.

The beagle dogs were divided into two groups and to each was administered one tablet after fasted. Blood was drawn from the forearm vein, respectively, 0.25, 0.5, 0.75, 1, 1.5, 2, 3 and 5 hours after the administration and measured for blood concentration of 5-FU. The measurement was made by the HPLC method (Yakugaku Zasshi, 105(11), 1058–1064, 1985). The results are shown in FIG. 8.

The sustained release effect using the hemicellulose was also confirmed by the above results obtained in a in vivo experiment.

What is claimed is:

1. A sustained release composition containing a pharmaceutically active agent in a matrix and having the sustained release rate controlled by incorporating at least 10% by weight of the matrix based on the total weight of the composition, in which the matrix is a hemicellulose extracted from wheat bran under alkaline conditions and purified by ultrafiltration and by ion exchange, or a wheat bran extract containing the hemicellulose.

2. The composition of claim 1, wherein the hemicellulose is a freeze-dried product.

3. The composition of claim 1, wherein the hemicellulose is a dried ethanol precipitate product.

4. The composition of claim 1, wherein the pharmaceutically active agent is a drug selected from the group consisting of antiinflammatory and analgesic agents, antituberculous agents, coronary vasodilators, antihypertensive agents, vitamins and the like.

5. The composition of claim 1, which is in any form including solid preparations, semi-solid preparations and liquid preparations.

* * * * *